(12) United States Patent
Vyas et al.

(10) Patent No.: US 10,287,436 B2
(45) Date of Patent: May 14, 2019

(54) PROCESS FOR THE PREPARATION OF INDOCYANINE GREEN

(71) Applicant: DISHMAN CARBOGEN AMCIS LIMITED, Ahmedabad (IN)

(72) Inventors: Janmejay Rajnikant Vyas, Ahmedabad (IN); Himani Dhotre, Ahmedabad (IN); Narasimha Sarma, Ahmedabad (IN); Babulal R. Patel, Ahmedabad (IN); Dinesh Kumar Sharma, Ahmedabad (IN); Dilip N. Patel, Ahmedabad (IN); Ashish A. Soni, Ahmedabad (IN)

(73) Assignee: DISHMAN CARBOGEN AMCIS LIMITED, Ahmedabad (IN)

( * ) Notice: Subject to any disclaimer, the term of this patent is extended or adjusted under 35 U.S.C. 154(b) by 0 days.

(21) Appl. No.: 15/780,555

(22) PCT Filed: Nov. 29, 2016

(86) PCT No.: PCT/IB2016/057178
§ 371 (c)(1),
(2) Date: May 31, 2018

(87) PCT Pub. No.: WO2017/093889
PCT Pub. Date: Jun. 8, 2017

(65) Prior Publication Data
US 2018/0346728 A1    Dec. 6, 2018

(30) Foreign Application Priority Data

Dec. 1, 2015 (IN) .......................... 4536/MUM/2015

(51) Int. Cl.
*C09B 23/08* (2006.01)
*C09B 67/54* (2006.01)
*C09B 67/42* (2006.01)

(52) U.S. Cl.
CPC ........ *C09B 23/086* (2013.01); *C09B 67/0092* (2013.01); *C09B 67/0096* (2013.01)

(58) Field of Classification Search
CPC .......................... C09B 23/086; C09B 67/0092
See application file for complete search history.

(56) References Cited

U.S. PATENT DOCUMENTS

| 5,750,722 A | 5/1998 | Huynh |
| 6,448,008 B1 * | 9/2002 | Caputo .................. C07H 19/04 19/4 |
| 8,034,626 B2 * | 10/2011 | Scherninski ......... C07D 209/10 436/166 |

FOREIGN PATENT DOCUMENTS

CN          104130178 A      11/2014

OTHER PUBLICATIONS

Substance Record for SID 967 (2005) PubChem Open Chemistry Database (https://pubchem.ncbi.nlm.nih.gov/substance/967).

* cited by examiner

*Primary Examiner* — Golam M Shameem
(74) *Attorney, Agent, or Firm* — Volpe and Koenig, P.C.

(57) ABSTRACT

The present invention involves an improved process for the preparation of Indocyanine green of Formula (I) having high purity of about 99%, wherein the process comprises steps of reacting 1,1,2-trimethyl-1H-benzo[e]indole with 1,4-butane sulfone in boiling solvent to give 4-(1,1,2-trimethyl-1H-benzo[e]indolium-3-yl)butane-1-sulfonate. Followed by reacting 4-(1,1,2-trimethyl-1H-benzo[e]indolium-3-yl)butane-1-sulfonate of Formula (IV) and N-phenyl-N-((1E,3E,5E)-5-(phenylimino)penta-1,3-dienyl)acetamide of formula (V) in presence of sodium acetate and alcohol; and extracting the title compound formula (I) with an ester solvent.

Formula I

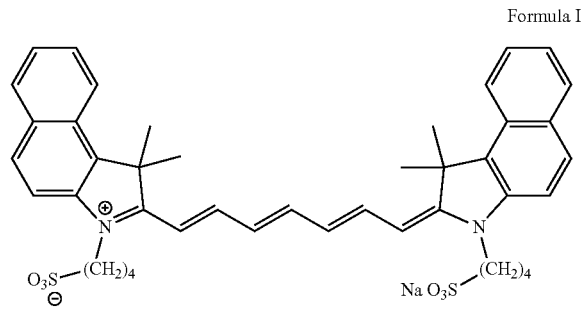

19 Claims, 1 Drawing Sheet

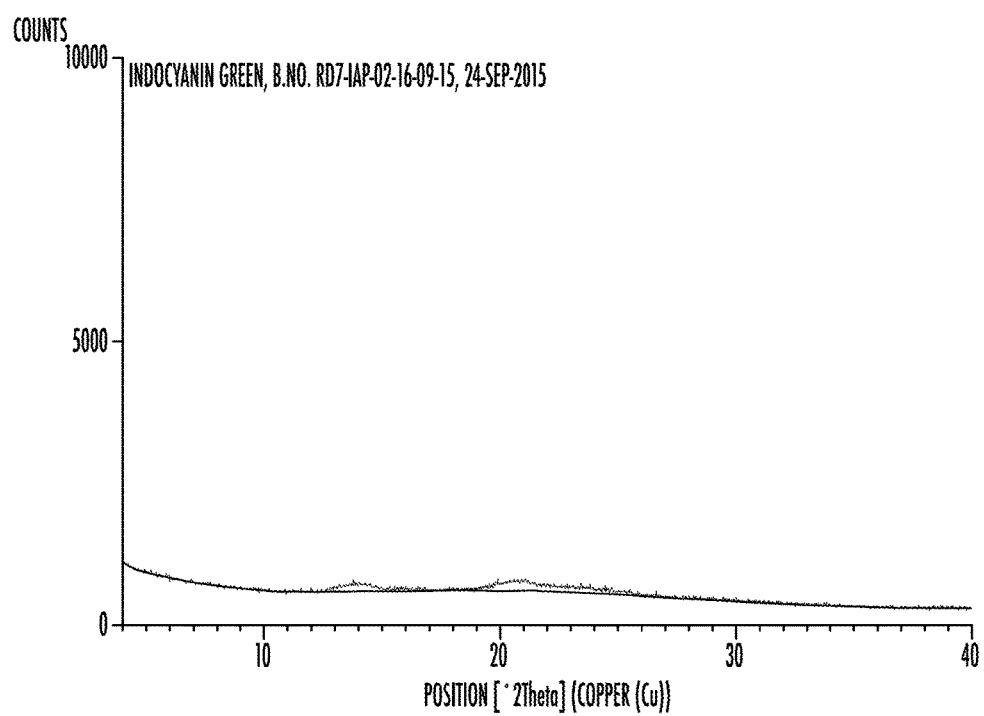

PROCESS FOR THE PREPARATION OF INDOCYANINE GREEN

CROSS REFERENCE TO RELATED APPLICATION

This application is a 35 USC § 371 national stage of PCT/IB2016/057178, which was filed Nov. 29, 2016 and claimed priority to IN 4536/MUM/2015, filed Dec. 1, 2015, both of which are incorporated herein by reference as if fully set forth.

FIELD OF INVENTION

The present invention provides a novel process for the preparation of stable amorphous form of Indocyanine green.

BACKGROUND OF THE INVENTION

Indocyanine green, chemically known as sodium 4-[2-[(1E,3E,5E,7Z)-7-[1,1-dimethyl-3-(4-sulfonatobutyl)benzo[e]indol-2-ylidene]hepta-1,3,5-trienyl]-1,1-dimethylbenzo[e] indol-3-ium-3-yl]butane-1-sulfonate, used in medical diagnostics. It is used for determining cardiac output, hepatic function, and liver blood flow, and for ophthalmic angiography.

Indocyanine green is a fluorescent dye which is used in medicine as an indicator substance (e.g. for photometric hepatic function diagnostics and fluorescence angiography) in cardiac, circulatory, hepatic and ophthalmic conditions. It is administered intravenously and, depending on liver performance, is eliminated from the body with a half life of approx. 3-4 minutes. Indocyanine green sodium salt is normally available in powder form and can be dissolved in various solvents; 5% (<5% depending on batch) sodium iodide is usually added to ensure better solubility. The sterile lyophilisate of a water-Indocyanine green solution is approved many European countries and the United States under the names Indocyanine green-Pulsion and Indocyanine green as a diagnostic for intravenous use.

U.S. Pat. No. 2,895,955 describes a structure including Indocyanine green and its pharmaceutically acceptable salts. Indocyanine green as its pharmaceutical acceptable salts [iodide disodium salt]. In accordance with the US'955 patent, Indocyanine green can prepared by reacting 1,1,2-trimethyl-1H-benzo[e]indole with 1,4-butane sultone in without solvent to produce 4-(1,1,2-trimethyl-1H-benzo[e]indolium-3-yl)butane-1-sulfonate, followed by treatment with N-phenyl-N-((1E,3E,5E)-5-(phenylimino)penta-1,3-dienyl)acetamide triethyl amine in ethanol and extraction in ether, and making sodium iodide salt in alcoholic solvent. In this process 4-(1,1,2-trimethyl-1H-benzo[e]indolium-3-yl)butane-1-sulfonate compound is not isolating or not easy filtration, also Indocyanine green not getting purity 99.0%.

According to PCT application WO2014/165216 patent, intermediate of N-((1E,3E,5E)-5-(phenylimino)penta-1,3-dien-1-yl) benzenaminium chloride treated with acetic anhydride in presence of triethylamine at −20° C. to give N-phenyl-N-((1E,3E,5E)-5-(phenylimino)penta-1,3-dienyl) acetamide, reaction carried out concentrated under high vacuum.

According to PCT application WO 2014192972 patent, intermediate of N-((1E,3E,5E)-5-(phenylimino)penta-1,3-dien-1-yl) benzenaminium chloride treated with acetic anhydride in presence of sodium acetate at 100° C. to give N-phenyl-N-((1E,3E,5E)-5-(phenylimino)penta-1,3-dienyl) acetamide, reaction 4-(1,1,2-trimethyl-1H-benzo[e] indolium-3-yl)butane-1-sulfonate in water.

U.S. Pat. No. 5,750,722 disclosed a process for preparing Indocyanine green acetone as purification solvent. And also US20090069573 patent purification solvent is methylene dichloride.

Wang, Dun; Jin, Wenshu; Qin, Enwei; Wang, Shuobing; Li, Peng Zhongguo Yiyao Gongye Zazhi Volume 37, Issue 9, Pages 584-585(2006) process for making indocyanine green.

Kundu, Kousik; Knight, Sarah F.; Willett, Nick; Lee, Sungmun; Taylor, W. Robert; Murthy, Niren Angewandte Chemie, International Edition Volume 48, Issue 2, Pages 299-303(2009) disclosed process for making Hydrocyanines: a class of fluorescent sensors that can image reactive oxygen species in cell culture, tissue, and in vivo.

According to PCT application WO2007/120579 patent describe process for making Indocyanine green as sodium iodide salt.

OBJECTIVE OF THE INVENTION

The main objective of the present invention is to provide an improved process for the preparation of Indocyanine green Yet another objective of the present invention is to provide an improved process for preparing a high purity NLT (Not Less Than) 98.0% of intermediate compound formula (IV).

Yet another objective of the present invention is to provide a simple and environmentally friendly process for the preparation of Indocyanine green, which avoids use of hazardous and expensive reagents.

Yet another objective of the present invention is to provide a process with a good yield and high purity NLT (Not Less Than) 99.0%

Yet another objective of the present invention is to provide an improved process for Indocyanine green, which is simple and industrially applicable.

SUMMARY OF INVENTION

In one aspect the present invention provides a novel and improved one-pot process for the preparation of sodium iodide Indocyanin green of Formula (I) having >99.0%

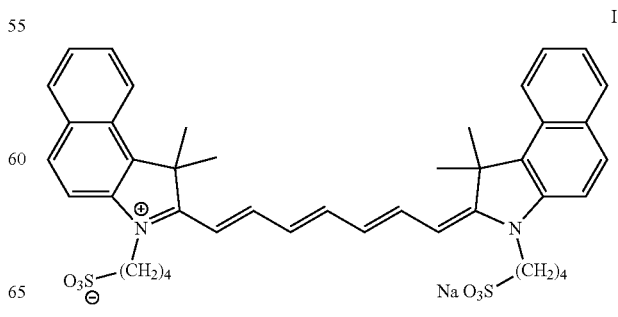

I said process comprises the steps of:

a) reacting 1,1,2-trimethyl-1H-benzo[e]indole Formula (II)

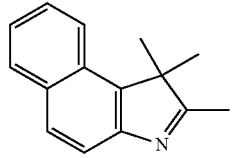

II with 1,4-butane sultone of Formula (III)

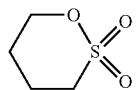

III in boiling solvent to give 4-(1,1,2-trimethyl-1H-benzo[e]indolium-3-yl)butane-1-sulfonate of Formula (IV);

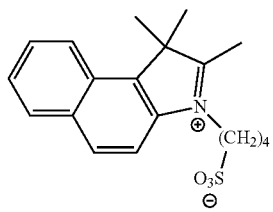

IV b) reacting 4-(1,1,2-trimethyl-1H-benzo[e]indolium-3-yl)butane-1-sulfonate of Formula (IV)

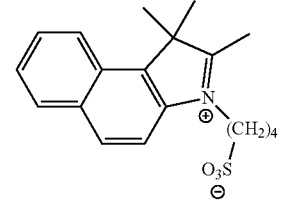

IV and N-phenyl-N-((1E,3E,5E)-5-(phenylimino)penta-1,3-dienyl)acetamide compound formula (V)

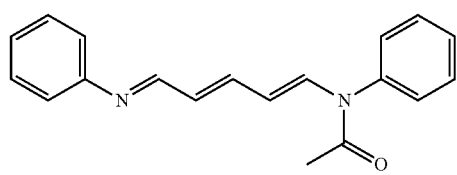

V in presence of sodium acetate and alcohol as solvent to give title compound formula (I).

In another aspect the present invention provides a process for preparation of the compound of formula (V)

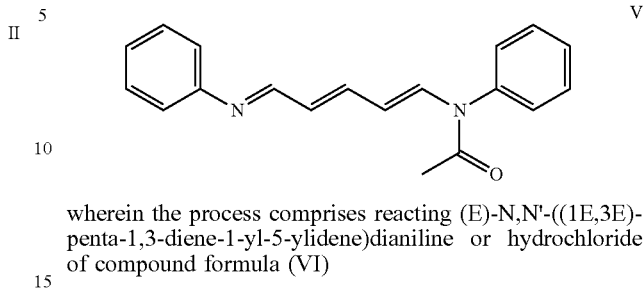

V wherein the process comprises reacting (E)-N,N'-((1E,3E)-penta-1,3-diene-1-yl-5-ylidene)dianiline or hydrochloride of compound formula (VI)

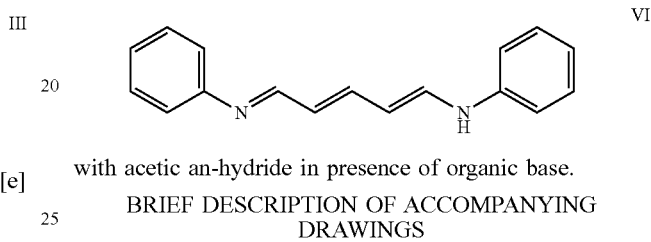

VI with acetic an-hydride in presence of organic base.

BRIEF DESCRIPTION OF ACCOMPANYING DRAWINGS

FIG-I: X-Ray Powder Diffraction (XRPD) pattern of Indocyanine green Formula (I) as a stable Amorphous form

DETAILED DESCRIPTION OF THE INVENTION

FIG. 1: X-Ray Powder Diffraction (XRPD) pattern of Indocyanine green' Formula (I) as a stable Amorphous form.

An improved process for the preparation of Indocyanine green of Formula (I) having >99.0% and without using sodium iodide.

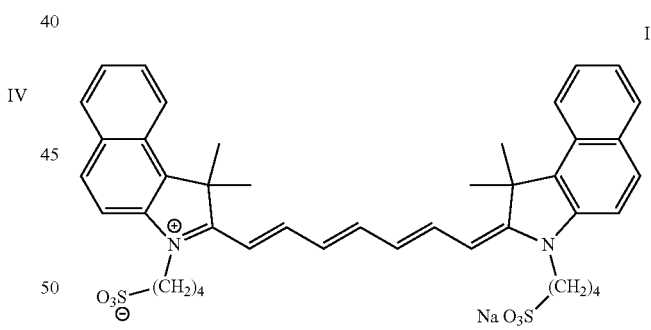

I condensation of the 4-(1,1,2-trimethyl-1H-benzo[e]indolium-3-yl)butane-1-sulfonate of Formula (IV)

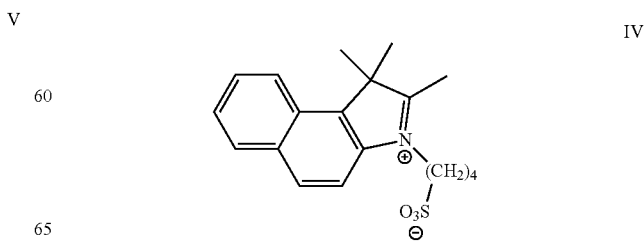

IV and N-phenyl-N-((1E,3E,5E)-5-(phenylimino)penta-1,3-dienyl)acetamide compound formula (V)

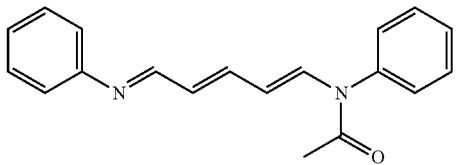

in presence of sodium acetate and alcohol as solvent followed by extraction using an extraction solvent to give title compound formula (I).

The condensation reaction is carried out in presence of alkali metal acetate salt, such as sodium, potassium, lithium salt of acetate, preferably sodium acetate.

The present invention is carried out in alcohol as solvent, alcohol solvent define as methanol, ethanol, isopropanol, n-butanol but preferably solvent is methanol.

It is carried out at temperature range about 50° C. to 90° C., but preferably temperature is 60° C. to 70° C.

The extraction is carried out in ester solvents such as ethyl acetate, isopropyl acetate, methyl acetate, preferably ethyl acetate.

The crude compound purification reaction is usually run in a suitable ketonic solvent such as water or a mixture of water and a ketonic solvent such as acetone, methyl ethyl ketone, preferably solvent is acetone and water.

According to the present invention compound of formula (IV) is prepared

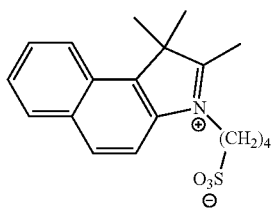

using the 1,1,2-trimethyl-1H-benzo[e]indole compound formula (II) and 1,4-butane sultone compound formula (III)

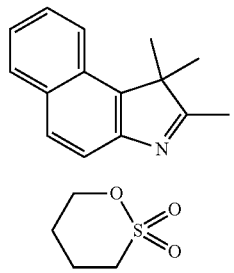

in high boiling solvent to give 4-(1,1,2-trimethyl-1H-benzo[e]indolium-3-yl)butane-1-sulfonate of Formula (IV)

The solvents used in the reaction between compound of formula II and compound of formula III is selected from toluene, xylene, hexane, sulfolene, silicone oil but preferably solvent is sulfolene.

The reaction for preparing compound formula (IV) reaction is carried out at temperature range from about 110° C. to about 180° C., preferably in the temperature range from 120° C. to 140° C.

The present invention also provides a process for the preparation of the compound formula (V)

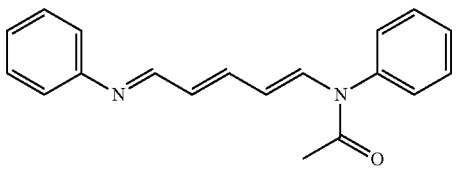

Wherein the process comprises reacting (E)-N,N'-(1E,3E)-penta-1,3-diene-1-yl-5-ylidene)dianiline or hydrochloride of compound formula (VI)

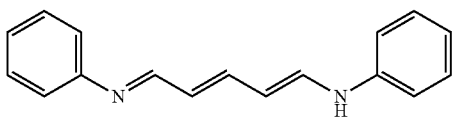

with acetic an-hydride in presence of organic base.

The preparation of compound of formula (V) reaction is carried out in an organic base such as primary amine, secondary, tertiary amine, methyl amine, ethyl amine, dimethyl amine, triethyl amine, preferably triethyl amine.

The solvent can also be selected from chlorinated solvent such as methylene dichloride, ethylene dichloride, preferably solvent is methylene dichloride.

The temperature range for carrying out the preparation of compound of formula V is from about 0° C. to about 30° C., preferably a temperature range from 0° C. to 5° C.

Throughout the description and claims the word "comprise" and variations of the word are not intended to exclude other technical features, additives, components, or steps. The content of the abstract of the present application is incorporated herein as reference. Additional objects, advantages and features of the invention will become apparent to those skilled in the art upon examination of the description or may be learned by practice of the invention. The following examples are provided by way of illustration, and is not intended to be limiting of the present invention.

Example-1

Preparation of 4-(1,1,2-trimethyl-1H-benzo[e]indolium-3-yl)butane-1-sulfonate 1,1,2-trimethyl-1H-benzo[e]indole (100 gm, 1.0 equivalent) was suspended in sulfolane (100 ml, 1.0 vol) and 1,4-Buane sultone was added and mixture was heated to 120-130° C. for 3-4 hrs, upon cooling to RT (Room temperature) add dichloromethane and stir for 4-5 hrs at 25-30° C. The mixture was filtered and the resulting solid was washed with dichloromethane. dried under vacuum and analyzed by HPLC (High performance liquid chromatography) (153 g, 92.0 percent). Having HPLC more than 98.0% Yield: 153 gm

Example-2

Preparation of N-phenyl-N-((1E,3E,5E)-5-(phenylimino)penta-1,3-dienyl)acetamide A solution of acetic anhydride (32.4 g, 3.6 equivalent) was added to a cooled (0-5° C.), stirred suspension of N-((1£, 3£',5Z)-5-(phenylimino)penta-1,3-dien-1-yl)benzen aminium chloride (25 g, 1.0 equivalent) and triethylamine (28.3 g, 4.47 equivalent) in CH$_2$Cl$_2$ (500 mL). The resulting clear solution was stirred for another 3 h at RT (Room temperature).

Add water and stir for 5 min, separated dichloromethane and concentrated under high vacuum. The residue containing N-phenyl-N-((1£,3 £',5Z)-5-(phenylimino)penta-1,3-dien-1-yl)acetamide to yield the title compound as an oily residue.

Yield: 25-26 gm (Oily liquid)
Chromatographic Purity (by TLC): ≥95 (% area),

Example-3

Preparation of Indocyanine Green

Charge methanol to the assembly at 25-30° C. and then charge 4-(1,1,2-trimethyl-1H-benzo[e]indolium-3-yl)butane-1-sulfonate (56.17 g 1.95 equivalent) and anhydrous sodium acetate (35.1 g, 2.6 Equivalent) stir solution for 5 min, then heat to reflux (65-70° C.) and maintain for 15-30 min. Then added solution of N-phenyl-N-((1E,3E,5E)-5-(phenylimino)penta-1,3-dienyl)acetamide (25 gm) in methanol (25 ml) at reflux temperature (65-70° C.). Reaction progress monitored by TLC (Thin layer chromatography) or HPLC 4-(1,1,2-trimethyl-1H-benzo[e]indolium-3-yl)butane-1-sulfonate NMT (Not More Than) −1.0%. After completion of reaction cool to 25-30° C. and Charge 1000 ml ethyl acetate and stir for 6 hrs at 25-30° C. Filter and wash with 50 ml ethyl acetate. The desired product was obtained as a green colour crystalline powder (46-50.5 gm, 80%). Having HPLC purity more than >98.0%.

Purification of Indocyanine Green

Example: 1

Add DM 315 ml water to the assembly at 25-30° C. and then add 45 g Indocyanine green (1.0 equivalent), heat to 55-60° C. And add 900 ml acetone and reflux for 1 hr. gradually cool to RT (Room temperature) and stir for 12 hrs at 25-30° C. Filter and wash with acetone. The desired product was obtained as a green colour crystalline powder (25 to 35 gm). Having HPLC purity more than >99.0%. XRPD pattern of powder diffractogram of Indocyanine green (FIG. 1).

Example: 2

Add DM (DE-mineralization water) 315 ml water to the assembly at 25-30° C. and then add 45 g Indocyanine green (1.0 equivalent) and sodium iodide (0.9 g, 2.0% w/w), heat to 55-60° C. and add 900 ml acetone and reflux for 1 hr. gradually cool to RT (Room temperature) and stir for 12 hrs at 25-30° C. Filter and wash with acetone The desired product was obtained as a green color crystalline powder (25 to 35 gm). Having HPLC purity more than >99.0%.

Example: 3

Add acetonitrile to the assembly at 25-30° C. and then add 45 g Indocyanine green (1.0 equivalent), heat to 55-60° C. And reflux for 1 hr. gradually cool to RT (Room temperature) and stir for 2-3 hrs at 25-30° C. Filter and wash with acetone. The desired product was obtained as a green colour crystalline powder (25 to 35 gm). Having HPLC purity more than >99.0%.

The invention claimed is:

1. A process for preparation of Indocyanine green of Formula (I) having high purity,

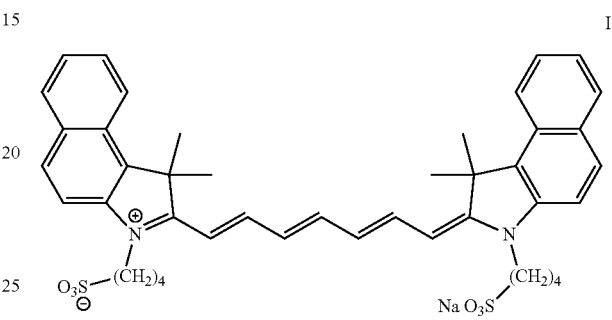

I wherein the process comprises steps of:
a) reacting 1,1,2-trimethyl-1H-benzo[e]indole of Formula (II)

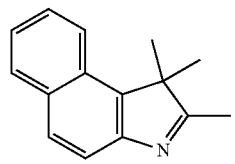

II with 1,4-butane sultone of Formula (III)

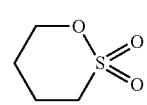

III in boiling solvent to give 4-(1,1,2-trimethyl-1H-benzo[e]indolium-3-yl)butane-1-sulfonate of Formula (IV);

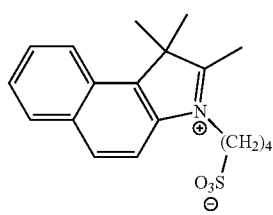

IV b) condensing 4-(1,1,2-trimethyl-1H-benzo[e]indolium-3-yl)butane-1-sulfonate of Formula (IV) and N-phenyl-N-((1E,3E,5E)-5-(phenylimino)penta-1,3-dienyl)acetamide of formula (V)

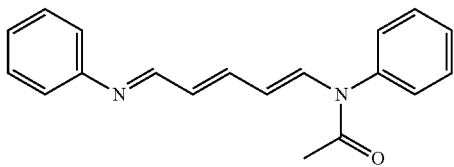

V in presence of sodium acetate and an alcohol; and c) extracting the Indocyanine green of formula (I) with an ester solvent.

2. The process according to claim 1, wherein preparation of the N-phenyl-N-((1E,3E,5E)-5-(phenylimino)penta-1,3-dienyl)acetamide of formula V comprises reacting (E)-N,N'-((1E,3E)-penta-1,3-diene-1-yl-5-ylidene)dianiline or hydrochloride of compound of formula (VI) with an acetic an-hydride in presence of an organic base

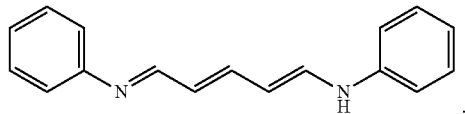

VI

.

3. The process according to claim 1, wherein the solvent in step-(a) is sulfolene, toluene, xylene or silicone oil.

4. The process according to claim 1, wherein the reaction in step-(a) is performed at a solvent reflux temperature ranging from 110° C. to 150° C.

5. The process according to claim 1, where the reaction in step-(b) is performed at a temperature range from 50° C. to solvent reflux temperature.

6. The process according to claim 1, wherein the alcohol in step-(b) is selected from methanol, ethanol, and isopropanol.

7. The process according to claim 1, wherein the ester solvent in step-(c) is methyl acetate or ethyl acetate.

8. The process according to claim 1, wherein the process comprises a further step of purification.

9. The process according to claim 8, wherein the purification is carried out in a solvent selected from $C_1$ to $C_5$ alcohols.

10. The process according to claim 8, wherein the purification is carried out in ketonic solvents.

11. The process according to claim 2, wherein the solvent is a chlorinated solvent.

12. The process according to claim 11, wherein the chlorinated solvent is methylene dichloride or ethylene dichloride.

13. The process according to claim 2, wherein the reaction is performed at a temperature range from room temperature to about 90° C.

14. The process according to claim 2, wherein the organic base is methyl amine, dimethyl amine, or triethyl amine.

15. The process according to claim 6, wherein the alcohol in step-(b) is methanol.

16. The process according to claim 7, wherein the ester solvent in step-(c) is ethyl acetate.

17. The process according to claim 10, wherein the Ketonic solvents are selected from acetone and acetonitrile in water.

18. The process according to claim 12, wherein the chlorinated solvent is methylene di-chloride.

19. The process according to claim 14, wherein the organic base is triethyl amine.

* * * * *